US008039650B2

(12) United States Patent
Kurashima et al.

(10) Patent No.: US 8,039,650 B2
(45) Date of Patent: Oct. 18, 2011

(54) PROCESS FOR PRODUCING TETRAGLYCIDYLAMINO COMPOUND

(75) Inventors: Hideharu Kurashima, Okayama (JP); Tsutomu Numoto, Okayama (JP); Jyunichi Hisae, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 12/597,920

(22) PCT Filed: May 8, 2008

(86) PCT No.: PCT/JP2008/058527
§ 371 (c)(1), (2), (4) Date: Oct. 28, 2009

(87) PCT Pub. No.: WO2008/140008
PCT Pub. Date: Nov. 20, 2008

(65) Prior Publication Data

US 2010/0222604 A1 Sep. 2, 2010

(30) Foreign Application Priority Data

May 8, 2007 (JP) ................................ 2007-123495

(51) Int. Cl.
*C07D 301/27* (2006.01)
*C07D 301/24* (2006.01)

(52) U.S. Cl. ......................... 549/522; 549/514; 549/520

(58) Field of Classification Search .................. 549/514, 549/520, 522
See application file for complete search history.

(56) References Cited

U.S. PATENT DOCUMENTS

| | | | |
|---|---|---|---|
| 4,487,948 | A | 12/1984 | Shimp et al. |
| 4,871,867 | A | 10/1989 | Hidaka et al. |

FOREIGN PATENT DOCUMENTS

| | | |
|---|---|---|
| JP | 59 175482 | 10/1984 |
| JP | 59 196314 | 11/1984 |
| JP | 8 32697 | 3/1996 |

*Primary Examiner* — Taylor Victor Oh
(74) *Attorney, Agent, or Firm* — Oblon, Spivak, McClelland, Maier & Neustadt, L.L.P.

(57) ABSTRACT

A diamine and an epihalohydrin are subjected to ring-opening addition reaction in the presence of water, to thereby produce a tetrahalohydrinamino compound (i.e., halohydrin compound). Thereafter, the halohydrin compound is reacted with an alkali metal hydroxide in the co-presence of a phase-transfer catalyst, to thereby allow cyclization reaction to proceed. An alkali metal halide by-produced during the cyclization reaction is dissolved in water and removed through phase separation. The resultant organic layer is washed with water for phase separation. Then, a crude tetraglycidylamino compound obtained by recovering unreacted epihalohydrin through evaporation is dissolved in an organic solvent and washed with water for phase separation. Subsequently, the organic solvent is recovered through evaporation under reduced pressure with heating, to thereby isolate a tetraglycidylamino compound (i.e., a product of interest). An aqueous alkali metal hydroxide solution is added to the organic solvent recovered through evaporation, followed by thermal treatment. The thus-purified organic solvent is recycled. This method can effectively produce, at low cost, a tetraglycidylamino compound (i.e., a product of interest) of reliable quality having low residual epihalohydrin and hydrolyzable halogen contents.

16 Claims, No Drawings

PROCESS FOR PRODUCING TETRAGLYCIDYLAMINO COMPOUND

TECHNICAL FIELD

The present invention relates to a method for producing a tetraglycidylamino compound from an aromatic or alicyclic diamine and an epihalohydrin. More particularly, the present invention relates to a method for effectively producing a tetraglycidylamino compound of reliable quality, which method realizes improvement in production efficiency and reduction in production cost.

BACKGROUND ART

Tetraglycidylamino compounds for producing useful as epoxy resins which exhibit low viscosity and good workability, and which give hardened products exhibiting excellent physical properties such as heat resistance, adhesion, rigidity, and mechanical strength. By virtue of these characteristic features, tetraglycidylamino compounds are used in a variety of fields and applications, including casting material, binder for carbon fiber composites, material used in the aerospace industry, material for electric and electronic parts, sporting goods, and polymer cross-linking agents.

Hitherto, there have been known methods for producing a tetraglycidylamino compound including a method in which a tetrahalohydrinamino compound having, on carbon atoms to each other, halogen and a hydroxyl group (hereinafter the compound may be referred to as a "halohydrin compound") is formed through ring-opening addition reaction between an aromatic or alicyclic diamine and an epihalohydrin, and subsequently a tetraglycidylamino compound is produced through cyclization reaction (ring-closure reaction) of the halohydrin compound.

Japanese Patent Publication (kokoku) No. H08-32697 (Patent Document 1) discloses a method for producing a tetraglycidylamino compound, including forming a halohydrin compound through reaction between an aromatic or alicyclic diamine and an epihalohydrin, and subsequently performing cyclization reaction of the halohydrin compound twice by use of a dehalogenating agent (e.g., an alkali metal hydroxide) in the co-presence of a phase-transfer catalyst, wherein washing with water is carried out before and after re-cyclization reaction. This method is provided for producing a tetraglycidylamino compound which is generally used in electric and electronic fields, and which contains a hydrolyzable halogen in a minimum possible amount.

However, in the procedure of the Examples described in Patent Document 1, an epihalohydrin is recovered, through evaporation, from a reaction product produced through cyclization reaction of a formed halohydrin compound in the co-presence of a phase-transfer catalyst; the evaporation residue containing a tetraglycidylamino compound is dissolved in an organic solvent; washing with water is carried out a plurality of times; and cyclization reaction of the halohydrin compound is carried out again in an organic solvent in the co-presence of a phase-transfer catalyst, followed by washing with water a plurality of times. The specification of Patent Document 1 describes that washing with water before re-cyclization reaction is an essential step, and prevents coloring of a final product and improves the storage stability thereof, and that when washing with water is carried out two or more times before re-cyclization reaction, the washing effect is improved.

Thus, the tetraglycidylamino compound production method described in Patent Document 1 requires an increased number of steps, a long-term process, and very intricate operations (e.g., phase separation), since cyclization reaction is performed twice and repeated washing with water is performed. In addition, the production method poses problems in that a tetraglycidylamino compound is lost and the yield thereof is reduced, due to a large amount of wastewater and repeated phase separation operations; i.e., the method involves reduction in production efficiency and an increase in production cost.

Through the method described in Patent Document 1, there can be produced a tetraglycidylamino compound containing a reduced amount of a hydrolyzable halogen. However, this patent document does not disclose recycle of an organic solvent used in a water washing (i.e., washing with water) step and re-cyclization reaction.

In the method described in Patent Document 1, when an organic solvent is disposed of in every batch process without being recycled, the organic solvent is consumed in a large amount, and thus production cost increases, leading to an economical disadvantage. In contrast, when an organic solvent recovered through evaporation is recycled as is, an epihalohydrin used is gradually accumulated in the organic solvent, and thus the residual epihalohydrin and hydrolyzable halogen contents of a product of interest increase gradually, which is problematic.

In the method described in Patent Document 1, an alkali metal halide by-produced during cyclization reaction is dissolved in water and removed through phase separation, and subsequently washing is carried out with a large amount of water (i.e., 15 mol on the basis of 1 mol of a diamine serving as a raw material). In this case, an epihalohydrin and a tetraglycidylamino compound are discharged to some extent together with water, and the amount of loss of the tetraglycidylamino compound is not negligible.

DISCLOSURE OF THE INVENTION

Problems to be Solved by the Invention

An object of the present invention is to solve the aforementioned problems involved in the conventional technique and to provide a method for effectively producing a tetraglycidylamino compound (i.e., a product of interest) of reliable quality having low residual epihalohydrin and hydrolyzable halogen contents.

Another object of the present invention is to provide a method for producing a tetraglycidylamino compound, which method realizes reduction in number of steps, shortening of process time, reduction in amount of wastewater, an increase in yield, reduction in loss of an epihalohydrin and a tetraglycidylamino compound, enhancement of production efficiency, and reduction in production cost.

Means for Solving the Problems

The present inventors have conducted extensive studies on tetraglycidylamino compound production methods involving the aforementioned problems, and as a result have found that the above-described objects can be attained through the following procedure: a diamine and an epihalohydrin are subjected to ring-opening addition reaction in the presence of water, to thereby produce a tetrahalohydrinamino compound (halohydrin compound); the halohydrin compound is reacted with an alkali metal hydroxide in the co-presence of a phase-transfer catalyst, to thereby allow cyclization reaction to proceed; an alkali metal halide by-produced during the cyclization reaction is dissolved in water and removed through phase separation; the resultant organic layer is washed with water for phase separation; a crude tetraglycidylamino compound obtained by recovering unreacted epihalohydrin through evaporation is dissolved in an organic solvent and washed with water for phase separation; the organic solvent is recovered through evaporation from the resultant organic layer under reduced pressure with heating, to thereby produce a tetraglycidylamino compound (i.e., a product of interest); an aqueous alkali metal hydroxide solution is added to the recovered organic solvent, followed by thermal treatment; and the thus-purified organic solvent is recycled. The present invention has been accomplished on the basis of this finding.

Accordingly, as described below, the present invention provides a method for producing a tetraglycidylamino compound.

1. A method for producing a tetraglycidylamino compound comprising forming a tetrahalohydrinamino compound through ring-opening addition reaction between a diamine represented by formula (1):

$$H_2NCH_2—R—CH_2NH_2 \quad (1)$$

(wherein R represents a phenylene group or a cyclohexylene group) and an epihalohydrin represented by formula (2):

$$\underset{\diagdown \,O\, \diagup}{CH_2—\overset{R'}{\overset{|}{C}}—CH_2X} \quad (2)$$

(wherein $R^1$ represents a hydrogen atom or a methyl group, and X represents a chlorine atom or a bromine atom) (hereinafter the tetrahalohydrinamino compound may be referred to as a "halohydrin compound"), and subjecting the halohydrin compound to cyclization reaction, to thereby produce a tetraglycidylamino compound represented by formula (3):

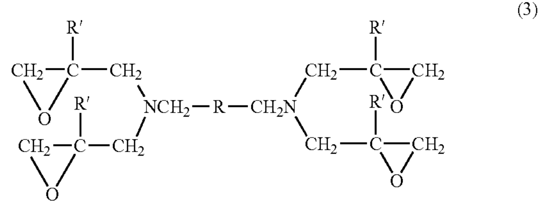

(wherein R represents a phenylene group or a cyclohexylene group, and $R^1$ represents a hydrogen atom or a methyl group), characterized in that the method comprises:

(A) a ring-opening addition reaction step of reacting a diamine represented by formula (1) with a stoichiometrically excess amount of an epihalohydrin represented by formula (2) in the presence of water, to thereby produce a halohydrin compound;

(B) a cyclization reaction step of reacting the halohydrin compound obtained in step (A) with an alkali metal hydroxide in the co-presence of a phase-transfer catalyst, to thereby produce a solution containing a tetraglycidylamino compound represented by formula (3);

(C) a step of adding water to the tetraglycidylamino-compound-containing solution obtained in step (B), to thereby dissolve, in water, an alkali metal halide by-produced during the cyclization reaction step, and removing an aqueous layer containing the alkali metal halide through phase separation, to thereby isolate an organic layer (1) containing the tetraglycidylamino compound and unreacted epihalohydrin;

(D) a step of washing the organic layer (1) obtained in step (C) with water, followed by phase separation, to thereby isolate an organic layer (2) containing the tetraglycidylamino compound and unreacted epihalohydrin;

(E) a step of recovering, through evaporation, unreacted epihalohydrin from the organic layer (2) obtained in step (D), to thereby isolate a crude tetraglycidylamino compound, dissolving the crude tetraglycidylamino compound in an organic solvent, and washing the resultant solution with water added thereto, followed by phase separation, to thereby isolate an organic layer (3) containing the tetraglycidylamino compound;

(F) a step of recovering, through evaporation, the organic solvent from the organic layer (3) obtained in step (E), to thereby isolate the tetraglycidylamino compound; and (G) a step of adding an aqueous alkali metal hydroxide solution to the organic solvent recovered through evaporation in step (F), and purifying the organic solvent under heating, wherein the organic solvent purified through step (G) is recycled.

2. A method for producing a tetraglycidylamino compound according to 1 above, wherein, in step (G), an aqueous alkali metal hydroxide solution is added to the organic solvent recovered through evaporation in step (F), and the resultant mixture is subjected to thermal treatment and then to phase separation, to thereby isolate the mixture into the purified organic solvent and an aqueous layer containing the alkali metal hydroxide.

3. A method for producing a tetraglycidylamino compound according to 1 above, wherein the organic solvent purified in step (G) is further filtered and then recycled.

4. A method for producing a tetraglycidylamino compound according to 1 above, wherein, in step (G), thermal treatment is carried out at 40 to 150° C.

5. A method for producing a tetraglycidylamino compound according to 1 above, wherein, in step (G), a phase-transfer catalyst is further added to the organic solvent recovered through evaporation in step (F), and the resultant mixture is subjected to thermal treatment.

6. A method for producing a tetraglycidylamino compound according to 1 above, wherein, in step (E), the solution obtained through dissolution in the organic solvent is washed only once with water.

7. A method for producing a tetraglycidylamino compound according to 1 above, wherein, in step (D), the amount of water employed for washing before phase separation is 0.5 to 5 mol on the basis of 1 mol of the diamine serving as a raw material.

8. A method for producing a tetraglycidylamino compound according to 1 above, wherein the organic solvent is an aromatic hydrocarbon or a cyclic fatty hydrocarbon.

9. A method for producing a tetraglycidylamino compound according to 8 above, wherein the organic solvent is toluene or m-xylene.

10. A method for producing a tetraglycidylamino compound according to 1 or 5 above, wherein the phase-transfer catalyst is a compound selected from the group consisting of an onium salt compound, a macrocyclic polyether compound, a linear polyether compound, and an aprotic polar compound.

11. A method for producing a tetraglycidylamino compound according to 1 above, wherein steps (A) to (G) are carried out in a batch process, and the entirety of the organic solvent purified through step (G) is recycled as at least a portion of the organic solvent employed in step (E) of the subsequent batch process.

Effects of the Invention

According to the method for producing a tetraglycidylamino compound of the present invention, there can effectively produced a tetraglycidylamino compound (i.e., a product of interest) of reliable quality having a residual epihalohydrin content of 100 ppm or less and a hydrolyzable halogen content of 600 ppm or less.

As compared with the conventional production method, the method for producing a tetraglycidylamino compound of the present invention achieves reduction in number of steps, shortening of process time, reduction in amount of wastewater, an increase in yield, reduction in loss of an epihalohydrin and a tetraglycidylamino compound, enhancement of production efficiency, and reduction in production cost.

BEST MODES FOR CARRYING OUT THE INVENTION

Steps of the method for producing a tetraglycidylamino compound of the present invention will next be described in detail.

Step (A)

In the method for producing a tetraglycidylamino compound of the present invention, firstly, in step (A), a tetrahalohydrinamino compound (halohydrin compound) is produced through ring-opening addition reaction between a diamine represented by formula (1) and an epihalohydrin represented by formula (2)

The diamine represented by formula (1) is generally m-xylylenediamine, p-xylylenediamine, a mixture thereof, 1,3-bis(aminomethyl)cyclohexane, 1,4-bis(aminomethyl)cyclohexane, or a mixture thereof, and is preferably m-xylylenediamine or 1,3-bis(aminomethyl)cyclohexane.

The epihalohydrin represented by formula (2) may be epichlorohydrin, epibromohydrin, or β-methylepichlorohydrin, and is preferably epichlorohydrin.

In step (A), a halohydrin compound is produced. Thus, stoichiometrically, 4 mol of an epihalohydrin is required on the basis of 1 mol of a diamine serving as a raw material.

However, since the epihalohydrin also serves as a solvent in step (A), the epihalohydrin is employed in a stoichiometrically excess amount with respect to the diamine serving as a raw material; i.e., the amount of the epihalohydrin is generally 5.5 to 15 mol, preferably 6.5 to 10 mol, on the basis of 1 mol of the diamine. When the amount of the epihalohydrin employed is 5.5 mol or more, an increase in viscosity can be suppressed in the reaction system during reaction or upon completion of reaction, resulting in easy handling, and coloring can be prevented in the reaction system. In contrast, when the amount of the epihalohydrin employed is 15 mol or less, a large reaction apparatus is not required, and an increase in cost of recovery of unreacted epihalohydrin is suppressed, which is economically advantageous.

The amount of water employed in step (A) is generally 0.5 to 15 mol, preferably 1 to 5 mol, on the basis of 1 mol of the diamine serving as a raw material. When the amount of water employed is 0.5 mol or more, addition reaction is promoted, which prevents precipitation of crystalline substances during addition of the diamine, and avoids difficulty in temperature control which would otherwise be caused by heat generation upon dissolution of the crystalline substances. In contrast, when the amount of water employed is 15 mol or less, there are prevented deterioration of the quality of a tetraglycidylamino compound (i.e., final product) due to side reactions, as well as an increase in loss of epihalohydrin.

Since the ring-opening addition reaction in step (A) is an exothermic reaction, the reaction is generally carried out by gradually adding the diamine to a mixture of the epihalohydrin and water so that the temperature of the reaction system does not exceed 60° C.

The reaction temperature is preferably 20 to 40° C. The reaction time after addition of the diamine is generally one to five hours, preferably two to three hours.

After completion of the ring-opening addition reaction in step (A), residual epihalohydrin may be recovered through evaporation under reduced pressure with heating so that the resultant halohydrin compound is not degraded.

Step (B)

In step (B), the halohydrin compound obtained in step (A) is reacted with an alkali metal hydroxide in the co-presence of a phase-transfer catalyst, to thereby produce a tetraglycidylamino compound through cyclization reaction of the halohydrin compound.

The alkali metal hydroxide employed in step (B) is generally sodium hydroxide or potassium hydroxide, and is preferably sodium hydroxide. The alkali metal hydroxide employed may be in the form of solid or aqueous solution. However, preferably, the alkali metal hydroxide is in the form of aqueous solution, from the viewpoint of easy handling. The aqueous sodium hydroxide solution employed is generally a commonly available 20 mass %, 25 mass %, or 48 mass % aqueous sodium hydroxide solution, and is particularly preferably a 48 mass % aqueous sodium hydroxide solution.

The amount of the alkali metal hydroxide employed in the cyclization reaction in step (B) is greater than 4 mol, which is the stoichiometric amount with respect to 1 mol of the diamine (raw material) employed in step (A). When the alkali metal hydroxide is employed in an excessively large amount, produced epoxy moieties may be consumed, or the epihalohydrin employed may be degraded. Therefore, the amount of the alkali metal hydroxide is generally 6 mol or less, preferably 4.2 to 5 mol, on the basis of 1 mol of the diamine serving as a raw material.

The phase-transfer catalyst employed in step (B) may be only one species selected from among compounds of the following groups (group 1 to group 4):

group 1: onium salt compound;

group 2: macrocyclic polyether compound;

group 3: linear polyether compound; and group 4: aprotic polar compound.

Specific examples of the onium salt compound of group 1 include quaternary ammonium salts such as tetramethylammonium chloride, tetraethylammonium chloride, tetrabutylammonium chloride, trilaurylmethylammonium chloride, benzyltrimethylammonium chloride, benzyltriethylammonium chloride, methyltrioctylammonium chloride, N-laurylpicolinium chloride, tetrabutylammonium bromide, tetrapropylammonium hydroxide, and tetrabutylammonium hydroxide; quaternary phosphonium salts such as tetramethylphosphonium chloride, tetraethylphosphonium chloride, tetrabutylphosphonium bromide, tribenzylethylphosphonium chloride, and tributylethylphosphonium chloride; and tertiary sulfonium salts such as trimethylsulfonium iodide and dibenzylmethylsulfonium bromide. Preferred are quaternary ammonium salts, and particularly preferred are benzyltrimethylammonium chloride and benzyltriethylammonium chloride.

Specific examples of the macrocyclic polyether compound of group 2 include crown ethers such as 12-crown-4, 15-crown-5, benzo-15-crown-5, 18-crown-6, dibenzo-18-crown-6, dicyclohexyl-18-crown-6, dibenzopyridino-18-crown-6, and dibenzo-24-crown-8; and cryptands such as diaza-15-crown, diaza-18-crown, [2,2,2]-cryptand, [2,2,1]1-cryptand, [2,1,1]-cryptand, [2,2,2]-decylcryptand, [2,2,2]-benzocryptand, Kryptofix 222B polymer, and Kryptofix 221B polymer.

"Kryptofix" is a trade name of cryptand distributed by Merck. Of these macrocyclic polyether compounds, crown ethers are preferably employed, with 18-crown-6 being particularly preferably employed.

Specific examples of the linear polyether compound of group 3 include polyalkylene oxides and terminally alkyletherified products thereof, such as polyethylene glycol, polyethylene glycol dimethyl ether, polyoxypropylene glycol, and polyoxypropylene glycol dimethyl ether; and polyether amines such as tris(3,6-dioxaheptyl)amine. Of these, polyalkylene oxides and terminally alkyletherified products thereof are preferably employed, with polyethylene glycol being particularly preferably employed.

Specific examples of the aprotic polar compound of group 4 include compounds which are known as so-called aprotic polar solvents, such as hexamethylphosphoric acid triamide, dimethyl sulfoxide, dimethylformamide, dimethylacetamide, acetonitrile, and N-methylpyrrolidone. Of these, hexamethylphosphoric acid triamide is preferably employed.

Of the aforementioned compounds of groups 1 to 4, quaternary ammonium salts of group 1 are preferably employed, with benzyltrimethylammonium chloride and benzyltriethylammonium chloride being particularly preferably employed.

The amount of the phase-transfer catalyst employed is generally 0.0001 to 0.05 mol, preferably 0.001 to 0.02 mol, more preferably 0.004 to 0.01 mol, on the basis of 1 mol of the diamine employed in step (A). The phase-transfer catalyst acts on an alkali metal hydroxide to thereby solubilize the alkali metal hydroxide in an organic layer. As a result, the alkali metal hydroxide can be transferred from the aqueous layer to the organic layer, to thereby promote the aforementioned cyclization reaction. When the amount of the phase-transfer catalyst employed is 0.0001 mol or more, the catalyst exhibits the effect of promoting the cyclization reaction. From the economic viewpoint, the phase-transfer catalyst is employed in an amount of 0.05 mol or less.

The cyclization reaction is an exothermic reaction, although the amount of heat generated in this reaction is smaller than that generated in the aforementioned ring-opening addition reaction. Therefore, the cyclization reaction is generally carried out by adding a phase-transfer catalyst to the halohydrin compound produced through ring-opening addition reaction in step (A), and then gradually adding an alkali metal hydroxide to the resultant mixture so that the temperature of the reaction system does not exceed 60° C. (preferably, the temperature falls within a range of 30 to 40° C.). The reaction time after addition of the alkali metal hydroxide—which may vary with the amount of the alkali metal hydroxide employed, or the specification (upper limit) of the hydrolyzable halogen content of a product of interest—is generally 0.5 to 5 hours, preferably 1 to 3 hours.

Step (C)

In step (C), water is added to the tetraglycidylamino-compound-containing solution obtained in step (B) (i.e., cyclization reaction step), to thereby dissolve, in water, an alkali metal halide by-produced during the cyclization reaction step, and an aqueous layer containing the alkali metal halide is removed through phase separation, to thereby isolate an organic layer (1) containing the tetraglycidylamino compound and unreacted epihalohydrin.

The amount of water employed for dissolving the alkali metal halide by-produced during the cyclization reaction step is preferably 27 to 33 mol on the basis of 1 mol of the diamine employed in step (A).

When the alkali metal halide by-produced during the cyclization reaction step is dissolved in water, and then the resultant mixture is allowed to stand still, the mixture is separated into an organic layer (1) containing the tetraglycidylamino compound and unreacted epihalohydrin and not containing the by-produced alkali metal halide, and an aqueous layer containing the by-produced alkali metal halide.

Step (D)

In step (D), the organic layer (1) obtained in step (C) is washed with water, followed by phase separation, to thereby isolate an organic layer (2) containing the tetraglycidylamino compound and unreacted epihalohydrin. Since a small amount of alkali metal hydroxide remains in the organic layer (1), when unreacted epihalohydrin is recovered through evaporation under heating without performing the above washing with water and phase separation, an epihalohydrin polymer may be produced, which causes loss of epihalohydrin. The epihalohydrin polymer exhibits water solubility, but may be deposited on a reactor. Therefore, deposition of the polymer on the reactor cannot be prevented without thorough washing with water, which is not preferred.

In step (D), washing is preferably carried out with water in an amount of 0.5 to 5 mol (more preferably 1 to 3 mol) on the basis of 1 mol of the diamine employed in step (A). When water is employed in an amount of 0.5 mol or more, production of an epihalohydrin polymer can be suppressed, whereas when water is employed in an amount of 5 mol or less, the amount of loss of epihalohydrin or a tetraglycidylamino compound due to dissolution thereof in water can be reduced.

The organic layer (1) is washed with the aforementioned amount of water under stirring, and then the resultant mixture is allowed to stand still, whereby the mixture is separated into the organic layer (2) and an aqueous layer.

Step (E)

In step (E), unreacted epihalohydrin is recovered, through distillation, from the organic layer (2) obtained in step (D), and a crude tetraglycidylamino compound is obtained through the bottom of the distillation column. The crude tetraglycidylamino compound is dissolved in an organic solvent, and the resultant solution is further washed with water, followed by phase separation, to thereby isolate an organic layer (3) containing the tetraglycidylamino compound.

The aforementioned recovery of unreacted epihalohydrin is carried out through evaporation under reduced pressure with heating so that the evaporation temperature does not exceed 100° C. (preferably 90° C.). The epihalohydrin recovered through evaporation may be recycled in step (A).

In step (E), an organic solvent is employed for dissolving the crude tetraglycidylamino compound therein for viscosity reduction, and enhancement of efficiency in washing with water. There is selected an organic solvent which has a specific gravity lower than that of water, which is inactive to the tetraglycidylamino compound, which dissolves the tetraglycidylamino compound, and which exhibits substantially no compatibility with water.

The organic solvent employed in step (E) is an aromatic hydrocarbon or a cyclic fatty hydrocarbon. Specific examples include toluene, o-xylene, m-xylene, p-xylene, mixed xylene, benzene, ethylbenzene, mesitylene, cyclohexane, and methylcyclohexane. Of these, toluene and m-xylene are particularly preferably employed. These organic solvents may be employed in combination of two or more species.

The amount of the organic solvent employed is generally 1 to 20 mol, preferably 3 to 7 mol, on the basis of 1 mol of the diamine (raw material) employed in step (A).

After the crude tetraglycidylamino compound has been dissolved in an organic solvent, the solution is washed with water for phase separation. The amount of water employed in this washing is generally 5 to 30 mol, preferably 10 to 20 mol, on the basis of 1 mol of the diamine (raw material) employed in step (A). From the viewpoints of reduction in number of steps, shortening of process time, and reduction in amount of wastewater, the solution is washed with water only once, which is enough for the purpose of this step.

Step (F)

In step (F), the organic solvent is recovered, through evaporation, from the organic layer (3) obtained in step (E), to thereby isolate the tetraglycidylamino compound.

Recovery of the organic solvent is carried out through evaporation under reduced pressure with heating so that the evaporation temperature is 110° C. or lower (preferably 100° C. or lower).

The organic solvent recovered through evaporation in step (F) contains the epihalohydrin which has not been completely recovered through evaporation in step (E). When this organic solvent is recycled as is, the epihalohydrin is gradually accumulated in the recovered organic solvent, and the residual epihalohydrin and hydrolyzable halogen contents of a product of interest increase gradually. Therefore, the organic solvent is purified in the subsequent step (G).

Step (G)

In step (G), an aqueous alkali metal hydroxide solution is added to the organic solvent recovered through evaporation, and the organic solvent is purified through thermal treatment.

Through this thermal treatment, the epihalohydrin contained in the organic solvent recovered through evaporation is converted into a polyhydric alcohol (e.g., glycerin) or an epihalohydrin polymer. Since such a polyhydric alcohol exhibits water solubility, the alcohol can be removed by dissolving it in an aqueous alkali metal hydroxide solution.

The epihalohydrin polymer is produced in the form of powder. Therefore, when a product of interest is required to have transparency, preferably, the polymer is removed through filtration of the thermally treated organic solvent.

The organic solvent recovered through evaporation may contain water co-boiled with the organic solvent, which water has not been completely removed through phase separation in step (E). The water is removed in step (G) or in step (E) of the subsequent batch process during purification treatment.

In step (G), a phase-transfer catalyst similar to that employed in step (B) may be added for promoting conversion of the epihalohydrin into a polyhydric alcohol, or production of an epihalohydrin polymer.

The aqueous alkali metal hydroxide solution employed in step (G) is similar to that employed in the cyclization reaction in step (B). The aqueous alkali metal hydroxide solution is preferably an aqueous sodium hydroxide solution, particularly preferably a 20-mass % aqueous sodium hydroxide solution. When a 48-mass % aqueous sodium hydroxide solution is employed in the cyclization reaction, the 48-mass % aqueous sodium hydroxide solution may be appropriately diluted with water and employed in step (G).

No particular limitation is imposed on the amount of the aqueous alkali metal hydroxide solution added in step (G), so long as the amount of the alkali metal hydroxide exceeds the amount of the epihalohydrin contained in the organic solvent recovered through evaporation. The amount of the alkali metal hydroxide is generally 1 to 20 mol, preferably 2 to 10 mol, particularly preferably 4 to 8 mol, on the basis of 1 mol of the epihalohydrin contained in the organic solvent recovered through evaporation.

The temperature of thermal treatment after addition of the aqueous alkali metal hydroxide solution, which may vary with the type of the organic solvent employed, is generally 40 to 150° C., preferably 60 to 100° C. When the thermal treatment temperature is 40° C. or higher, the epihalohydrin contained in the organic solvent recovered through evaporation is converted into a polyhydric alcohol or an epihalohydrin polymer. In contrast, when the thermal treatment temperature is 150° C. or lower, the organic solvent can be recycled in the subsequent batch process without requiring long-term cooling, which is economically advantageous.

No particular limitation is imposed on the pressure during thermal treatment, and no problem arises even when thermal treatment is carried out under pressurized conditions. However, generally, thermal treatment is carried out at ambient pressure, since the cost of a reaction vessel increases when thermal treatment is performed under pressurized conditions, which is economically disadvantageous.

The thermal treatment time, which may vary with the type of the organic solvent employed and the heating temperature, is generally 0.5 to 5 hours, preferably 1 to 3 hours. When the thermal treatment time is 0.5 hours or longer, the epihalohydrin contained in the organic solvent recovered through evaporation is converted into a polyhydric alcohol or an epihalohydrin polymer. In contrast, when the thermal treatment time is 5 hours or shorter, upon recycle of the organic solvent in the subsequent batch process, problems due to insufficient cooling time do not arise in a production cycle, which is economically advantageous.

The alkali metal hydroxide, polyhydric alcohol, etc. contained in the organic solvent purified through thermal treatment dissolve in water. Therefore, when the purified organic solvent is recycled in step (E) of the subsequent batch process, the alkali metal hydroxide, polyhydric alcohol, etc. are removed through washing with water and phase separation in the same step. However, preferably, the above-recovered and thermally treated organic solvent is subjected to phase separation, to thereby separate the resultant mixture into the purified organic solvent and an aqueous layer containing the alkali metal hydroxide.

The thus-purified organic solvent can be recycled repeatedly. Generally, steps (A) to (G) are carried out in a batch process, and the organic solvent purified through step (G) is recycled in step (E) of the subsequent batch process.

The entirety of the organic solvent recovered through evaporation can be recycled by subjecting the organic solvent to the above-described purification treatment in step (G), including conversion of epihalohydrin into a polyhydric alcohol or an epihalohydrin polymer, dissolution of the polyhydric alcohol in an aqueous alkali metal hydroxide solution, removal of the polyhydric alcohol through phase separation, or removal of the epihalohydrin polymer through filtration.

As described above, the recovered organic solvent is purified through step (G) (in which an aqueous alkali metal hydroxide solution is added to the organic solvent, followed by thermal treatment, and then wastewater containing the alkali metal hydroxide is removed through phase separation), and the thus-purified organic solvent is recycled. Through the procedure, a tetraglycidylamino compound having residual epihalohydrin and hydrolyzable halogen contents which are generally maintained at low level is produced in every batch process, and the level is almost constant. In step (G), in which the recovered organic solvent is thermally treated with an aqueous alkali metal hydroxide solution, a small amount of the organic solvent is lost, and the amount of loss corresponds to about 1 to about 5 mass % of the amount of the initially employed organic solvent. The loss of the organic solvent is compensated by an organic solvent newly added in the subsequent or later batch processes.

The purified tetraglycidylamino compound obtained in step (F) of the method of the present invention has residual epihalohydrin and hydrolyzable halogen contents which are maintained at low level, shows a pale color (Gardner color scale: 1 or less), has a low viscosity of 1,500 to 2,500 mPa·s (25° C.), and exhibits a suppressed increase in viscosity during storage. The tetraglycidylamino compound has a specification sufficient for a variety of applications, including a material for casting, a binder for carbon fiber composites, a material for the aerospace industry, sporting goods, a polymer cross-linking agent, and an adhesive.

EXAMPLES

The present invention will next be described in detail with reference to Examples and Comparative Examples. However, the present invention is not limited to these Examples.

The tetraglycidylamino compounds produced in the below-described Examples, and the organic solvents recovered and purified therein were evaluated through the following methods.

(1) Hydrolyzable Chlorine

A tetraglycidylamino compound (0.5 g) was precisely weighed and dissolved in a 1/10N potassium hydroxide-methanol solution (20 mL). Thereafter, chlorine generated through hydrolysis at 70° C. for 15 minutes was potentiometrically titrated with a (1/250)N aqueous silver nitrate solution, to thereby determine hydrolyzable chlorine concentration.

(2) Viscosity

Viscosity was measured at 25° C. by means of a TV-20 viscometer (cone-plate type, product of Toki Sangyo Co., Ltd.).

(3) Gardner Color Scale

Gardner color scale was measured according to JIS K 5600-2-1 (1999).

(4) Storage Stability (viscosity Increasing Factor)

A tetraglycidylamino compound was heated at 100° C. for 24 hours, and the viscosity of the thus-heated compound was measured. Viscosity increasing factor was determined by comparing the thus-measured viscosity with the initial viscosity of the compound, and the thus-determined viscosity increasing factor was employed for evaluation of storage stability. The lower the viscosity increasing factor, the better the storage stability.

(5) Residual Epichlorohydrin Concentration of Product and Recovered Organic Solvent A tetraglycidylamino compound (i.e., a product of interest) or a recovered organic solvent was dissolved in acetone, and the resultant solution was analyzed by gas chromatography using m-xylene as an internal standard substance. A gas chromatograph GC-17A (product of Shimadzu Corporation) with a capillary column HR-1 (product of Shinwa Chemical Industries Ltd., 0.32 mmϕ×25 m) was employed.

(6) Purity of Purified Organic Solvent

A purified organic solvent was dissolved in acetone, and the resultant solution was analyzed by gas chromatography using m-xylene as an internal standard substance. A gas chromatograph GC-17A (product of Shimadzu Corporation) with a capillary column HR-1 (product of Shinwa Chemical Industries Ltd., 0.32 mmϕ×25 m) was employed.

GC-17A (product of Shimadzu Corporation) was employed as a gas chromatograph, and HR-1 (product of Shinwa Chemical Industries Ltd., 0.32 mmϕ×25 m) was employed as a capillary column.

Example 1

Step (A): Epichlorohydrin (740.2 g, 8 mol) and water (36.0 g, 2 mol) were added to a 2-L reactor equipped with a cooler, a heater, and a stirrer, and the temperature of the reaction mixture was elevated to 35° C. while nitrogen was caused to flow through the reaction system. While the temperature of the reaction mixture was maintained at 35° C., m-xylylenediamine (136.2 g, 1 mol) was added dropwise thereto over one hour. Then, the reaction temperature was further maintained at 35° C. for two hours, to thereby complete addition reaction.

Step (B): Subsequently, a 50-mass % aqueous benzyltriethylammonium chloride solution (3.64 g, 0.008 mol as benzyltriethylammonium chloride) was added to the reaction mixture. Thereafter, while the temperature of the reaction mixture was maintained at 35° C., a 48% aqueous sodium hydroxide solution (400.0 g, 4.8 mol as sodium hydroxide) was added dropwise thereto over 30 minutes. Then, the reaction temperature was further maintained at 35° C. for two hours, to thereby allow cyclization reaction to proceed.

Step (C): After completion of cyclization reaction, water (540.5 g, 30 mol) was added to the reaction mixture, to thereby dissolve, in water, sodium chloride by-produced during cyclization reaction, and the resultant mixture was allowed to stand still for one hour for phase separation. Wastewater containing sodium chloride was removed, to thereby isolate an organic layer (1).

Step (D): Subsequently, the organic layer (1) was washed with water (54.0 g, 3 mol), followed by phase separation, to thereby isolate an organic layer (2).

Step (E): The organic layer (2) was subjected to distillation under reduced pressure (0.67 kPa (absolute pressure)), and excess epichlorohydrin was recovered through evaporation at 85 to 90° C. over three hours, to thereby isolate crude tetraglycidyl-m-xylylenediamine.

The thus-obtained crude tetraglycidyl-m-xylylenediamine was added to and dissolved in toluene (645.0 g, 7 mol), and the resultant solution was washed with water (270.2 g, 15 mol). Thereafter, the resultant mixture was allowed to stand still for one hour for phase separation, and the aqueous layer containing, for example, water-soluble organic matter was removed, to thereby isolate an organic layer (3) containing tetraglycidyl-m-xylylenediamine.

Step (F): The organic layer (3) was subjected to distillation under reduced pressure (0.67 kPa (absolute pressure)) at 95 to 100° C. over three hours, and toluene (664.0 g) containing about 3 mass % water and 0.6 mass % epichlorohydrin was recovered through evaporation. The thus-separated tetraglycidyl-m-xylylenediamine was cooled and then filtered through a 50-mesh SUS screen, to thereby yield 353.2 g of purified tetraglycidyl-m-xylylenediamine (i.e., a product of interest) (yield on the basis of m-xylylenediamine: 98.0%).

The purified tetraglycidyl-m-xylylenediamine obtained in the 1st batch process was analyzed. The results are as follows: residual epichlorohydrin: 35 ppm, hydrolyzable chlorine: 410 ppm, viscosity: 1,630 mPa·s, Gardner color scale: 1, and storage stability (viscosity increasing factor): 1.17.

The total time required for the 1st batch process (including working time) was 19 hours.

Step (G): Subsequently, a 20 mass % aqueous sodium hydroxide solution (34.4 g) (i.e., an aqueous solution containing sodium hydroxide in an amount of four times by mole that of epichlorohydrin contained in the above-recovered toluene) was added to the recovered toluene, and the resultant mixture was thermally treated at 90° C. for one hour. The mixture was cooled to 35° C., and the aqueous layer containing sodium hydroxide was separated therefrom. Thereafter, the resultant organic layer was filtered through filter paper (ADVANTEC 5A), to thereby recover purified toluene (626.0 g, purity: 99.0 mass %). The thus-purified toluene was employed in step (E) of the subsequent batch process. The amount of loss of toluene was found to be 25.3 g (3.9%). Epichlorohydrin was not detected in the thus-purified toluene (detection limit: 10 ppm).

In the second or later batch processes, synthesis of tetraglycidyl-m-xylylenediamine was repeated by carrying out steps (A) to (F) and step (G) (i.e., thermal treatment of recovered toluene) in a manner similar to that described above, and compensating the loss of toluene so that the amount of toluene fed to step (E) was adjusted to 7 mol.

Table 1 shows average yield (on the basis of m-xylylenediamine) and the average percent recovery of epichlorohydrin in the 1st to 20th batch processes, as well as the properties of a product of interest produced in each batch process.

As is clear from Table 1, the residual epichlorohydrin or hydrolyzable chlorine content of products produced in the 20 batch processes is maintained at almost the same level, and the viscosity, Gardner color scale, and storage stability of the product of each of the 2nd to 20th batch processes are similar to those of the product of the 1st batch process.

Examples 2 to 4

The procedure of Example 1 was repeated, except that conditions for thermal treatment of recovered toluene were changed as shown in Table 1, to thereby produce tetraglycidyl-m-xylylenediamine (i.e., a product of interest).

Table 1 shows average yield (on the basis of m-xylylenediamine) and the average percent recovery of epichlorohydrin in the 1st to 20th batch processes, as well as the properties of a product of interest produced in each batch process.

Example 5

The procedure of Example 1 was repeated, except that toluene was replaced with m-xylene, and recovered m-xylene was thermally treated at 100° C. with an aqueous sodium hydroxide solution, to thereby produce tetraglycidyl-m-xylylenediamine (i.e., a product of interest).

Table 1 shows average yield (on the basis of m-xylylenediamine) and the average percent recovery of epichlorohydrin in the 1st to 20th batch processes, as well as the properties of a product of interest produced in each batch process.

Example 6

The procedure of Example 1 was repeated, except that m-xylylenediamine was replaced with 1,3-bis(aminomethyl) cyclohexane, to thereby produce tetraglycidyl-1,3-bis(aminomethyl)cyclohexane (i.e., a product of interest).

Table 1 shows average yield (on the basis of 1,3-bis(aminomethyl)cyclohexane) and the average percent recovery of epichlorohydrin in the 1st to 20th batch processes, as well as the properties of a product of interest produced in each batch process.

Examples 7 and 8

The procedure of Example 1 was repeated, except that the amount of water employed in washing in step (D) was changed as shown in Table 1, to thereby produce tetraglycidyl-m-xylylenediamine.

Table 1 shows average yield (on the basis of m-xylylenediamine) and the average percent recovery of epichlorohydrin in the 1st to 20th batch processes, as well as the properties of a product of interest produced in each batch process.

Comparative Example 1

An experiment was carried out according to Example 1 described in Patent Document 1.

Epichlorohydrin (740.2 g, 8 mol) and water (36.0 g, 2 mol) were added to a 2-L reactor equipped with a cooler, a heater, and a stirrer, and the temperature of the reaction mixture was elevated to 35° C. while nitrogen was caused to flow through the reaction system. While the temperature of the reaction mixture was maintained at 35° C., m-xylylenediamine (136.2 g, 1 mol) was added dropwise thereto over one hour. Then, the reaction temperature was further maintained at 35° C. for two hours, to thereby complete ring-opening addition reaction. Subsequently, a 50 mass % aqueous benzyltriethylammonium chloride solution (3.64 g, 0.008 mol as reduced to benzyltriethylammonium chloride) was added to the reaction mixture. Thereafter, while the temperature of the reaction mixture was maintained at 35° C., a 48 mass % aqueous sodium hydroxide solution (400.0 g, 4.8 mol as reduced to sodium hydroxide) was added dropwise thereto over minutes. Then, the reaction temperature was further maintained at 35° C. for two hours, to thereby allow cyclization reaction to proceed.

After completion of cyclization reaction, water (540.5 g, 30 mol) was added to the reaction mixture, to thereby dissolve, in water, sodium chloride by-produced during cyclization reaction, and the resultant mixture was allowed to stand still for one hour for phase separation. Wastewater containing sodium chloride was removed, to thereby isolate an organic layer (1). Thereafter, the organic layer (1) was washed with water (54.0 g, 3 mol) for phase separation (water washing 1), to thereby isolate an organic layer (2).

Subsequently, excess epichlorohydrin was removed through evaporation from the organic layer (2) under reduced pressure (0.67 kPa (absolute pressure)) at 85 to 90° C. over three hours, to thereby obtain an evaporation residue (1).

The evaporation residue (1) was added to and dissolved in toluene (645.0 g, 7 mol), and the resultant solution was washed twice with water (270.2 g, 15 mol) for phase separation (water washing 2-1 and water washing 2-2). Water washing for phase separation (twice) and removal of wastewater required a long period of time (total: four hours) and very intricate operations. To the organic layer obtained through water washing and phase separation were added potassium hydroxide (3.9 g, 0.07 mol), water (15.6 g, 0.87 mol, i.e., an amount corresponding to a 20 mass % aqueous potassium hydroxide solution), hexamethylphosphoric acid triamide (12.5 g, 0.07 mol) serving as a phase-transfer catalyst, and polyethylene glycol (2.8 g, 0.007 mol). Then, the reaction temperature was maintained at 35° C. for two hours, to thereby allow re-cyclization reaction to proceed. After separation of the aqueous layer containing potassium hydroxide and the phase-transfer catalyst, the resultant organic layer was washed twice with water (270.2 g, 15 mol) for phase separation (water washing 3-1 and water washing 3-2). Water washing for phase separation (twice) and removal of wastewater required a long period of time (total: four hours) and very intricate operations. Toluene was recovered through evaporation from the organic layer under reduced pressure (0.67 kPa (absolute pressure)) at 95 to 100° C. over three hours. Thus, toluene (646.0 g) containing about 3 mass % water was recovered. The thus-recovered toluene was found to contain epichlorohydrin in an amount of 0.5 mass %. Tetraglycidyl-m-xylylenediamine obtained in the form of evaporation residue was cooled and then filtered through a 50-mesh SUS screen for removal of foreign matter, to thereby yield 331.6 g of purified tetraglycidyl-m-xylylenediamine (i.e., a product of interest) (yield on the basis of m-xylylenediamine: 92.0%). The total time required for the entire process (including working time) was 28 hours.

The thus-obtained tetraglycidyl-m-xylylenediamine was analyzed. The results are as follows: hydrolyzable chlorine: 120 ppm, viscosity: 1,680 mPa·s, Gardner color scale: 1, and storage stability (viscosity increasing factor): 1.28.

In the second or later batch processes, synthesis of tetraglycidyl-m-xylylenediamine was repeated under the same synthesis conditions as those described above by recycling recovered toluene as is, and compensating the loss of toluene so that the amount of fed toluene was adjusted to 7 mol.

As shown in Table 2, since epichlorohydrin was accumulated in recovered toluene, the residual epichlorohydrin and hydrolyzable chlorine concentrations of a product of interest increased as the number of batch processes increased.

Table 2 shows the average percent recovery of epichlorohydrin in the 1st to 20th batch processes, as well as the properties of a product of interest produced in each batch process.

The average percent recovery of epichlorohydrin was 83.0%, which is almost equal to that in the case of Example 1 (i.e., 84.2%). However, as shown in Table 2, epichlorohydrin was accumulated in recovered toluene. Therefore, the residual epichlorohydrin and hydrolyzable chlorine concentrations of a product of interest increased as the number of batch processes increased.

Comparative Example 2

The procedure of Comparative Example 1 was repeated, except that the amount of water employed in water washing 1 was changed to 0.3 mol, to thereby yield tetraglycidyl-m-xylylenediamine (i.e., a product of interest).

Table 2 shows average yield (on the basis of m-xylylenediamine) and the average percent recovery of epichlorohydrin in the 1st to 20th batch processes, as well as the properties of a product of interest produced in each batch process.

Since the amount of water employed in water washing 1 was insufficient, an epichlorohydrin polymer was generated after recovery of epichlorohydrin and deposited on the reactor. The epichlorohydrin polymer solidified and became difficult to remove as at the number of repetition of synthesis increased. Due to generation of the epichlorohydrin polymer, the average percent recovery of epichlorohydrin was 78.4%, which is lower than that in the case of Example 1.

Comparative Example 3

The procedure of Comparative Example 1 was repeated, except that the amount of water employed in water washing 1 was changed to 15 mol (as in the case of Example 1 described in Patent Document 1), to thereby yield tetraglycidyl-m-xylylenediamine (i.e., a product of interest).

Table 2 shows average yield (on the basis of m-xylylenediamine) and the average percent recovery of epichlorohydrin in the 1st to 20th batch processes, as well as the properties of a product of interest produced in each batch process.

Since a large amount of water was employed in water washing 1, the loss of epichlorohydrin increased, and the average percent recovery of epichlorohydrin was 73.6%, which is lower than that in the case of Example 1.

Comparative Example 4

The procedure of Comparative Example 1 was repeated, except that m-xylylenediamine was replaced with 1,3-bis(aminomethyl)cyclohexane, to thereby yield tetraglycidyl-1,3-bis(aminomethyl)cyclohexane (i.e., a product of interest).

Table 2 shows average yield (on the basis of 1,3-bis(aminomethyl)cyclohexane) and the average percent recovery of epichlorohydrin in the 1st to 20th batch processes, as well as the properties of a product of interest produced in each batch process.

TABLE 1

| | Ex. 1 | Ex. 2 | Ex. 3 | Ex. 4 | Ex. 5 | Ex. 6 | Ex. 7 | Ex. 8 |
|---|---|---|---|---|---|---|---|---|
| Raw material diamine | MXDA | MXDA | MXDA | MXDA | MXDA | 1,3-BAC | MXDA | MXDA |
| Organic solvent | TOL | TOL | TOL | TOL | MX | TOL | TOL | TOL |
| Amount of water used in water washing (g) | | | | | | | | |
| (1) Step (D) | 54.0 | 54.0 | 54.0 | 54.0 | 54.0 | 54.0 | 5.4 | 270.2 |
| (2) Step (E) | 270.2 | 270.2 | 270.2 | 270.2 | 270.2 | 270.2 | 270.2 | 270.2 |
| Total amount of water used | 324.2 | 324.2 | 324.2 | 324.2 | 324.2 | 324.2 | 275.6 | 540.4 |
| Thermal treatment of recovered organic solvent | | | | | | | | |
| (1) Amount of NaOH used (*) | 4.0 | 4.0 | 8.0 | 12.0 | 4.0 | 4.0 | 4.0 | 4.0 |
| (2) Heating temperature (° C.) | 90 | 70 | 70 | 50 | 100 | 90 | 90 | 90 |
| (3) Thermal treatment time (Hr) | 1 | 1 | 3 | 3 | 1 | 1 | 1 | 1 |
| Average product yield (%) | 98.0 | 98.2 | 98.3 | 98.0 | 97.7 | 97.2 | 98.4 | 97.5 |
| Average percent recovery of ECH (%) | 84.2 | 82.9 | 84.4 | 85.2 | 83.7 | 82.0 | 77.3 | 73.4 |
| Properties of product | | | | | | | | |
| (1) Residual ECH (ppm) | | | | | | | | |
| Batch 1 | 35 | 70 | 40 | 80 | 20 | 40 | 45 | 35 |
| Batch 2 | 45 | 65 | 50 | 90 | 25 | 35 | 35 | 30 |
| Batch 3 | 40 | 70 | 45 | 90 | 20 | 40 | 40 | 35 |
| Batch 5 | 45 | 60 | 55 | 85 | 30 | 35 | 35 | 40 |

TABLE 1-continued

| | Ex. 1 | Ex. 2 | Ex. 3 | Ex. 4 | Ex. 5 | Ex. 6 | Ex. 7 | Ex. 8 |
|---|---|---|---|---|---|---|---|---|
| Batch 7 | 40 | 75 | 45 | 85 | 25 | 45 | 35 | 40 |
| Batch 9 | 35 | 65 | 50 | 90 | 30 | 40 | 40 | 40 |
| Batch 12 | 40 | 60 | 40 | 80 | 15 | 40 | 45 | 35 |
| Batch 15 | 40 | 70 | 45 | 85 | 20 | 45 | 45 | 35 |
| Batch 20 | 35 | 65 | 40 | 85 | 15 | 45 | 35 | 30 |
| (2) Hydrolyzable chlorine (ppm) | | | | | | | | |
| Batch 1 | 410 | 430 | 415 | 435 | 390 | 550 | 415 | 385 |
| Batch 2 | 430 | 435 | 425 | 440 | 400 | 570 | 425 | 395 |
| Batch 3 | 415 | 425 | 420 | 435 | 410 | 550 | 395 | 400 |
| Batch 5 | 425 | 435 | 425 | 430 | 405 | 560 | 390 | 395 |
| Batch 7 | 410 | 435 | 435 | 440 | 395 | 545 | 410 | 390 |
| Batch 9 | 390 | 430 | 430 | 440 | 400 | 550 | 405 | 400 |
| Batch 12 | 425 | 425 | 410 | 420 | 385 | 565 | 405 | 405 |
| Batch 15 | 420 | 420 | 415 | 430 | 395 | 555 | 395 | 390 |
| Batch 20 | 425 | 430 | 415 | 425 | 400 | 550 | 390 | 385 |

TABLE 2

| | Comp. Ex. 1 | Comp. Ex. 2 | Comp. Ex. 3 | Comp. Ex. 4 |
|---|---|---|---|---|
| Raw material diamine | MXDA | MXDA | MXDA | 1,3-BAC |
| Organic solvent | TOL | TOL | TOL | TOL |
| Amount of water used in water washing (g) | | | | |
| (1) Water washing 1 | 54.0 | 5.4 | 270.2 | 54.0 |
| (2) Water washing 2-1 | 270.2 | 270.2 | 270.2 | 270.2 |
| (3) Water washing 2-2 | 270.2 | 270.2 | 270.2 | 270.2 |
| (4) Water washing 3-1 | 270.2 | 270.2 | 270.2 | 270.2 |
| (5) Water washing 3-2 | 270.2 | 270.2 | 270.2 | 270.2 |
| Total amount of water used | 1134.8 | 1086.2 | 1351.0 | 1134.8 |
| Average product yield (%) | 92.0 | 92.2 | 91.2 | 90.2 |
| Average percent recovery of ECH (%) | 83.0 | 78.4 | 73.6 | 81.0 |
| Properties of product | | | | |
| (1) Residual ECH (ppm) | | | | |
| Batch 1 | 35 | 40 | 35 | 35 |
| Batch 2 | 140 | 145 | 150 | 135 |
| Batch 3 | 240 | 240 | 245 | 230 |
| Batch 5 | 450 | 460 | 470 | 465 |
| Batch 7 | 640 | 645 | 650 | 650 |
| Batch 9 | 855 | 865 | 860 | 880 |
| Batch 12 | 1160 | 1170 | 1150 | 1150 |
| Batch 15 | 1440 | 1480 | 1455 | 1450 |
| Batch 20 | 1990 | 2000 | 1985 | 1980 |
| (2) Hydrolyzable chlorine (ppm) | | | | |
| Batch 1 | 120 | 130 | 120 | 250 |
| Batch 2 | 160 | 170 | 165 | 300 |
| Batch 3 | 205 | 210 | 220 | 335 |
| Batch 5 | 300 | 305 | 310 | 425 |
| Batch 7 | 380 | 395 | 390 | 505 |
| Batch 9 | 470 | 495 | 500 | 590 |
| Batch 12 | 595 | 610 | 620 | 705 |
| Batch 15 | 710 | 720 | 730 | 830 |
| Batch 20 | 900 | 915 | 920 | 1040 |

In Tables 1 and 2, "MXDA" represents m-xylylenediamine, "1,3-BAC" 1,3-bis(aminomethyl)cyclohexane, "MX" m-xylene, "TOL" toluene, and "ECH" epichlorohydrin.

"Amount of NaOH used (*)" in thermal treatment of a recovered organic solvent corresponds to the amount by mole of NaOH on the basis of 1 mol of epichlorohydrin contained in the organic solvent. "Average yield" or "Average percent recovery of ECH" is the average of data obtained in the 1st to 20th batch processes.

The products of Comparative Examples 1 to 4 were produced through the method described in Patent Document 1. The method described in Patent Document 1 differs from the method for producing a tetraglycidylamino compound of the present invention mainly in the following points.

In the present invention, although step (G) (i.e., step of purifying a recovered organic solvent) is required, the water washing (phase separation) step—which is employed in the method described in Patent Document 1 and requires a large amount of water—is greatly simplified, and thus the amount of wastewater to be disposed is considerably reduced. For example, the total amount of water employed in Example 1 is about 29% of that of water employed in Comparative Example 1. Thus, in the present invention, the amount of water for washing and the amount of wastewater are considerably reduced, as compared with the case of the method described in Patent Document 1.

The method of the present invention does not require re-cyclization reaction using a phase-transfer catalyst and an alkali metal hydroxide. Therefore, although the method described in Patent Document 1 requires 28 hours for one batch process, the present invention requires only 19 hours for one batch process; i.e., the working time is reduced by nine hours for one batch process. In the present invention, step (G) requires three to five hours. However, step (G) can be carried out in parallel with steps (A) to (D), or in parallel with steps (A) to (F) (when the recovered organic solvent is stored), and thus the time required for step (G) is not included in the working time.

In the products of the Comparative Examples, which are produced through the method described in Patent Document 1, the residual epichlorohydrin concentration (i.e., product property (1)) is low in the first batch process, but increases as the number of batch processes increases. In contrast, in the products of the Examples, which are produced through the method of the present invention, residual epichlorohydrin concentration is maintained at a low level even when the number of batch processes increases.

Similar to the case of the residual epichlorohydrin concentration, in the products of the Comparative Examples, which are produced through the method described in Patent Document 1, the hydrolyzable chlorine concentration (i.e., product property (2)) is low in the first batch process, but increases as the number of batch processes increases. In contrast, in the products of the Examples, which are produced through the method of the present invention, the hydrolyzable chlorine concentration is maintained at a low level even when the number of batch processes increases, although the concentration is higher than that of products produced in early batch processes in the Comparative Examples.

In the method of the present invention, residual epichlorohydrin contained in a recovered organic solvent is removed through purification of the organic solvent. Therefore, the residual epichlorohydrin and hydrolyzable chlorine concentrations of a product of interest (i.e., a tetraglycidylamino compound) do not increase even when the number of batch processes increases, and the tetraglycidylamino compound exhibits reliable quality.

In Comparative Example 1, the experiment was carried out in a similar manner as employed in Example 1 described in Patent Document 1. However, for example, the amount of water employed in the step of "water washing 1" is not necessarily strictly equal to that in the case of Example 1 described in Patent Document 1. Therefore, data obtained in Comparative Example 2 or 3 correspond to the case where the amount of water employed in water washing 1 is considerably changed. Similarly, data obtained in Example 7 or 8 correspond to the case where the amount of water employed in step (D) is considerably changed.

The amount of water employed in water washing 1 in Comparative Example 2 or in step (D) in Example 7 is 5.4 g (i.e., 0.3 mol on the basis of 1 mol of a diamine serving as a raw material), and the amount of water employed in water washing 1 in Comparative Example 3 or in step (D) in Example 8 is 270.2 g (i.e., 15 mol on the basis of 1 mol of a diamine serving as a raw material). Since such an amount of water employed falls outside a preferred range of the amount of water employed in step (D) (i.e., 0.5 to 5 mol on the basis of 1 mol of a diamine serving as a raw material), the loss of epichlorohydrin (ECH) increases, and the average percent recovery of ECH is reduced. However, in Example 7 or 8, the residual epichlorohydrin and hydrolyzable chlorine concentrations of a product of interest are maintained at a low level. These data indicate that the amount of water employed in step (D) does not correlate with the properties of a product of interest, and that a product with excellent properties is reliably produced through the method of the present invention.

The amount of water employed in Example 7 is about 25% that of water employed in Comparative Example 2, and the amount of water employed in Example 8 is about 40% that of water employed in Comparative Example 3. Thus, the amount of water employed is reduced in each Example.

As described hereinabove, according to the method of the present invention, a tetraglycidylamino compound of high quality is consistently produced, the number of intricate steps of water washing and phase separation is reduced, and the working time is considerably reduced (by about 30%), as compared with the case of the method described in Patent Document 1. Therefore, the method of the present invention realizes enhancement of production efficiency.

According to the method of the present invention, since the amount of water employed in water washing and the amount of wastewater are considerably reduced, costs for water employed and treatment of wastewater are reduced.

The method of the present invention requires cyclization reaction of a halohydrin compound only once. Therefore, the amount of a phase-transfer catalyst or alkali metal hydroxide employed for the reaction is reduced.

According to the method of the present invention, loss of a tetraglycidylamino compound or epichlorohydrin—which would otherwise occur in association with water washing or phase separation—is suppressed.

According to the present invention, since a recovered organic solvent is purified through thermal treatment, the organic solvent can be repeatedly used many times, and residual epichlorohydrin or hydrolyzable chlorine is not accumulated in a tetraglycidylamino compound (i.e., a product of interest). Thus, the present invention realizes considerable reduction in amount of an organic solvent consumed.

Thus, the present invention effectively produces a tetraglycidylamino compound of reliable quality, and realizes reduction in number of steps, shortening of process time, reduction in amount of wastewater, and an increase in yield. Therefore, the present invention realizes enhancement of production efficiency, and reduction in production cost.

The invention claimed is:

1. A method for producing a tetraglycidylamino compound comprising forming a tetrahalohydrinamino compound through a ring-opening addition reaction between a diamine represented by formula (1):

$$H_2NCH_2—R—CH_2NH_2 \quad (1)$$

in which R represents a phenylene group or a cyclohexylene group, and an epihalohydrin represented by formula (2):

$$\underset{\diagdown\ \ \diagup \atop O}{CH_2—\overset{R'}{\overset{|}{C}}}—CH_2X \quad (2)$$

in which $R^1$ represents a hydrogen atom or a methyl group, and X represents a chlorine atom or a bromine atom, hereinafter referred to as a halohydrin compound, and subjecting the halohydrin compound to a cyclization reaction, to thereby produce a tetraglycidylamino compound represented by formula (3):

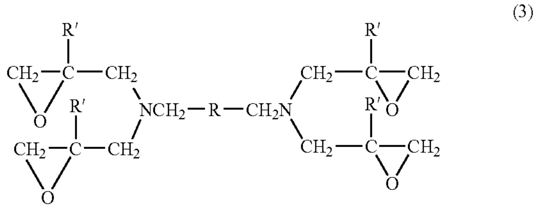

in which R represents a phenylene group or a cyclohexylene group, and $R^1$ represents a hydrogen atom or a methyl group, wherein the method comprises:

(A) a ring-opening addition reaction comprising reacting a diamine represented by formula (1) with a stoichiometrically excess amount of an epihalohydrin represented by formula (2) in the presence of water, to thereby produce a halohydrin compound;

(B) a cyclization reaction comprising reacting the halohydrin compound obtained in (A) with an alkali metal hydroxide in the co-presence of an onium salt compound, to thereby produce a first solution including a tetraglycidylamino compound represented by formula (3);

(C) adding water to the first solution obtained in (B), to thereby dissolve, in water, an alkali metal halide by-produced during the cyclization reaction, and removing an aqueous layer including the alkali metal halide through phase separation, to thereby isolate an organic layer (1) including the tetraglycidylamino compound and unreacted epihalohydrin;

(D) washing the organic layer (1) obtained in (C) with water, followed by phase separation, to thereby isolate an organic layer (2) including the tetraglycidylamino compound and unreacted epihalohydrin;

(E) recovering, through evaporation, unreacted epihalohydrin from the organic layer (2) obtained in (D), to thereby isolate a crude tetraglycidylamino compound, dissolving the crude tetraglycidylamino compound in an organic solvent, and washing the resultant solution with water added thereto, followed by phase separation, to thereby isolate an organic layer (3) including the tetraglycidylamino compound;

(F) recovering, through evaporation, the organic solvent from the organic layer (3) obtained in (E), to thereby isolate the tetraglycidylamino compound; and (G) adding an aqueous alkali metal hydroxide solution to the organic solvent recovered through evaporation in (F), and purifying the organic solvent through a thermal treatment, wherein the organic solvent purified through (G) is recycled.

2. The method for producing a tetraglycidylamino compound according to claim 1, wherein, in (G), an aqueous alkali metal hydroxide solution is added to the organic solvent recovered through evaporation in (F), and the resultant mixture is subjected to the thermal treatment and then to phase separation, to thereby isolate the mixture into the purified organic solvent and an aqueous layer including the alkali metal hydroxide.

3. The method for producing a tetraglycidylamino compound according to claim 1, wherein the organic solvent purified in (G) is further filtered and then recycled.

4. The method for producing a tetraglycidylamino compound according to claim 1, wherein, in (G), the thermal treatment is carried out at 40 to 150° C.

5. The method for producing a tetraglycidylamino compound according to claim 1, wherein, in (G), the onium salt compound is further added to the organic solvent recovered through evaporation in (F), and the resultant mixture is subjected to the thermal treatment.

6. The method for producing a tetraglycidylamino compound according to claim 1, wherein, in (E), the solution obtained through the dissolution in the organic solvent is washed only once with water.

7. The method for producing a tetraglycidylamino compound according to claim 1, wherein, in (D), the amount of water employed for washing before phase separation is 0.5 to 5 mol on the basis of 1 mol of the diamine serving as a raw material.

8. The method for producing a tetraglycidylamino compound according to claim 1, wherein the organic solvent is an aromatic hydrocarbon or a cyclic fatty hydrocarbon.

9. The method for producing a tetraglycidylamino compound according to claim 8, wherein the organic solvent is toluene or m-xylene.

10. The method for producing a tetraglycidylamino compound according to claim 1, wherein (A) to (G) are carried out in a batch process, and the entirety of the organic solvent purified through (G) is recycled as at least a portion of the organic solvent employed in (E) of the subsequent batch process.

11. The method for producing a tetraglycidylamino compound according to claim 1, wherein the onium salt compound is employed in an amount of 0.004 to 0.01 mol on a basis of 1 mol of the diamine employed in (A).

12. The method for producing a tetraglycidylamino compound according to claim 1, wherein the epihalohydrin is employed in (A) in an amount of 6.5 to 10 mol on a basis of 1 mol of the diamine serving as a raw material.

13. The method for producing a tetraglycidylamino compound according to claim 1, wherein the alkali metal is employed in (B) in an amount of 4.2 to 5 mol on a basis of 1 mol of the diamine serving as a raw material.

14. The method for producing a tetraglycidylamino compound according to claim 1, wherein the water is employed in (D) for washing before phase separation in an amount of 1 to 3 mol on the basis of 1 mol of the diamine serving as a raw material.

15. The method for producing a tetraglycidylamino compound according to claim 1, wherein the thermal treatment in (G) is carried out at 60 to 100° C.

16. The method for producing a tetraglycidylamino compound according to claim 1, wherein the thermal treatment in (G) is carried out for 1 to 3 hours.

* * * * *